(12) United States Patent
Hogg et al.

(10) Patent No.: US 9,345,813 B2
(45) Date of Patent: May 24, 2016

(54) THREE DIMENSIONAL PACKAGING FOR MEDICAL IMPLANTS

(75) Inventors: Andreas Hogg, Le Locle (CH); Yanik Tardy, Le Locle (CH); Thierry Aellen, Neuchatel (CH); Herbert Keppner, Colombier (CH); Juergen Burger, Le Locle (CH)

(73) Assignee: MEDOS INTERNATIONAL S.A.R.L. (CH)

( * ) Notice: Subject to any disclaimer, the term of this patent is extended or adjusted under 35 U.S.C. 154(b) by 0 days.

(21) Appl. No.: 13/491,081

(22) Filed: Jun. 7, 2012

(65) Prior Publication Data

US 2013/0330498 A1  Dec. 12, 2013

(51) Int. Cl.
| | |
|---|---|
| B05D 3/10 | (2006.01) |
| B32B 3/08 | (2006.01) |
| B32B 27/06 | (2006.01) |
| B32B 27/20 | (2006.01) |
| A61L 31/10 | (2006.01) |
| A61N 1/375 | (2006.01) |

(52) U.S. Cl.
CPC .................. *A61L 31/10* (2013.01); *A61N 1/375* (2013.01); *A61L 2420/02* (2013.01); *Y10T 428/239* (2015.01)

(58) Field of Classification Search
None
See application file for complete search history.

(56) References Cited

U.S. PATENT DOCUMENTS

| | | | |
|---|---|---|---|
| 6,456,812 B1 * | 9/2002 | Gervasi et al. | ................ 399/266 |
| 6,570,325 B2 | 5/2003 | Graff | |
| 6,709,715 B1 | 3/2004 | Lang | |
| 6,992,371 B2 * | 1/2006 | Mancini et al. | ............... 438/642 |
| 7,347,826 B1 | 3/2008 | Karicherla | |
| 7,364,925 B2 | 4/2008 | Lee | |
| 2002/0185712 A1 | 12/2002 | Stark | |
| 2005/0146267 A1 | 7/2005 | Lee | |
| 2005/0273146 A1 | 12/2005 | DeSimone | |
| 2006/0111791 A1 | 5/2006 | Forsell | |
| 2006/0173497 A1 | 8/2006 | Mech | |
| 2007/0216300 A1 | 9/2007 | Lee | |
| 2008/0051862 A1 * | 2/2008 | Mech et al. | ................... 607/116 |
| 2008/0200750 A1 | 8/2008 | James | |
| 2009/0263581 A1 | 10/2009 | Martin, III | |
| 2009/0263641 A1 | 10/2009 | Martin, III | |
| 2009/0291200 A1 | 11/2009 | Bedinger | |
| 2011/0015686 A1 | 1/2011 | Kara | |
| 2011/0038130 A1 | 2/2011 | Hogg | |
| 2011/0038131 A1 | 2/2011 | Hogg | |
| 2011/0039050 A1 | 2/2011 | Hogg | |

OTHER PUBLICATIONS

Oxford Dictionary, "Cement", Oxford Online Dictionary <http://oxforddictionaries.com/definition/english/cement?q=cement>.*
DuPont "Teflon AF®", DuPont webpage <http://www2.dupont.com/Teflon_Industrial/en_US/products/product_by_name/teflon_af/properties.html>.*

(Continued)

*Primary Examiner* — David Sample
*Assistant Examiner* — Donald M Flores, Jr.

(57) ABSTRACT

Implantable medical devices, and methods of coating same, including a plurality of components disposed on a substrate, and a low surface energy layer deposited as a liquid over at least a first portion of the components and the substrate, the low surface energy layer becoming solidified after deposition and conforming to at least the first portion of the components. The devices further include a biocompatible hermetic coating conforming to and sealingly covering at least a portion of the low surface energy layer.

16 Claims, 5 Drawing Sheets

(56) References Cited

OTHER PUBLICATIONS

Dupont "Teflon AF®—Figure 6 Modulus Plot", DuPont webpage <http://www2.dupont.com/Teflon_Industrial/en_US/assets/images/teflon_af_fig6.jpg>.*

Becker, K.F, et al; Film Coating—Large Area Encapsulation Process for Electronics Packaging; Polytronic 2005—5th International Conference on Polymers and Adhesives in Microelectronics and Photonics; 2005; pp. 30-33; USA.

Dow Corning; Information about Dow Corning® Brand Silicon Encapsulants; Product Information Brochure; 2000-2008; Dow Corning Corporation; USA.

Dow Corning; *Sylgard®* 184 Silicone Elastomer Curing Agent; Material Safety Data Sheet; 2008; pp. 1-8; Version 2.4; Dow Corning Corporation; USA.

Dow Corning; *Sylgard®* 184 Silicone Elastomer; Product Information Brochure; 2008; Dow Corning Corporation; USA.

Gill, I., et al; Bioencapsulation within synthetic polymers (Part 1): sol—gel encapsulated biological; Trends in Biotechnology; Jul. 1, 2000; pp. 282-296; vol. 18; No. 7, Cell Press; USA.

Mackenzie, John D.; Physical Properties of Sol-Gel Coatings; Journal of Sol-Gel Science and Technology; 2000; pp. 23-29; vol. 19; Kluwer Academic Publishers. The Netherlands.

Micro Resist Technolgoy GMBH; Oromocer®s (Hybrid Polymers) for Micro Optics; Product brochure; Jun. 23, 2008; pp. 1-4; Berlin, Germany.

Saegusa, T.; Organic-inorganic polymers hybrids; Pure &Appl. Chem., 1995, pp. 1965-1970, vol. 67, No. 12. Printed in Great Britain.

Vaeth, K., et al; Transition Metals for Selective Chemical Vapor Deposition of Parylene-Based Polymers; Chemistry of Materials, 2000; pp. 1305-1313; vol. 12, No. 5; 2000 American Chemical Society; Columbus, Ohio.

European Search Report EP13170792.9 dated Jan. 7, 2014.

* cited by examiner

THREE DIMENSIONAL PACKAGING FOR MEDICAL IMPLANTS

BACKGROUND OF THE INVENTION

1. Field of the Invention

The invention relates to hermetic biocompatible packaging and more particularly to an initial low surface energy layer deposited over three-dimensional structures.

2. Description of the Related Art

Packaging which is cost-effective and compatible with miniaturization is an important factor in the production of an implantable medical device. There is a need for a reliable, cost-effective batch-manufacturing packaging process such as a wafer level packaging to protect components such as electronic- and mechanical components, micro-electronic- and mechanical systems, micro-electro-mechanical systems and substrates carrying such components. The mentioned packaging must be mechanically and chemically stable to protect the body tissue from potentially toxic dissolvents and fragments, and also to protect the components of the implanted device from corrosion or degradation created by bodily fluids. Mechanical degradation mechanisms include swelling, wear, creep, and fatigue, while possible chemical mechanisms include oxidation and hydrolysis that may be accelerated by physiological ions, enzymes, or microbes.

Encapsulation of organic light emitting diodes by at least one barrier stack is disclosed in U.S. Pat. No. 6,570,325 by Graff et al. The barrier stack includes at least one barrier layer and at least one decoupling layer. Other protective barriers which include parylene for opto-electronic devices are disclosed by Lee et al. in U.S. Patent Application Publication Nos. 2005/0146267, now U.S. Pat. No. 7,364,925, and 2007/0216300, now abandoned.

Techniques for protecting integrated circuits using copolymers formed of parylene N and co-monomers with various double bonds is disclosed by Lang et al. in U.S. Pat. No. 6,709,715. Other coating techniques utilizing parylene are disclosed by Bedinger et al. in U.S. Patent Application Publication No. 2009/0291200 and by Martin, III et al. in U.S. Patent Application Publication Nos. 2009/0263581 and 2009/0263641.

Four of the present inventors also are also named inventors in U.S. Patent Application Publication Nos. 2011/0038130, 2011/0038131 and 2011/0039050, which are expressly incorporated herein by reference in their entireties. These currently pending applications disclose thin multi-layer hermetic packaging for complex topological structures such as medical devices having electronic components.

It is therefore desirable to provide improved hermetic biocompatible packaging, especially for implantable medical devices for which reduction of size is preferred.

SUMMARY OF THE INVENTION

An object of the present invention is to provide improved multi-layer packaging having low permeability to bodily fluids to protect both the patient and components beneath the packaging.

Another object of the present invention is to increase the conformity of multi-layer hermetic packaging for three-dimensional structures.

Yet another object of the present invention is to increase the mechanical stability of such packaging.

This invention features an implantable medical device including a plurality of components disposed on a substrate, and a low surface energy layer deposited as a liquid over at least a first surface of a first portion of the components and the substrate, the low surface energy layer becoming solidified after deposition. The low surface energy layer conforms to at least the first portion of the components. The device further includes a biocompatible hermetic coating conforming to and sealingly covering at least a portion of the low surface energy layer, and therefore conforming to and sealingly covering at least a portion of the components while overlying the low surface energy layer.

In a number of embodiments, the low surface energy layer exhibits surface reduction of a factor ranging between 1 to 100 compared to the first surface, and the low surface energy layer has Young's modulus lower than 50 GPa. In certain embodiments, the low surface energy layer rounds the volume of surface features for the three-dimensional portion to have an average minimal radius between 10 to 1000 microns, and the low surface energy layer has hardness lower than 20 Vickers. Preferably, the low surface energy layer exhibits less than twenty percent shrinkage during solidification.

In some embodiments, the low surface energy layer is selected from the group consisting of silicones, polyurethanes, gypsum, cements, epoxies, sol-gels, ethylene-vinyl acetate and mixtures thereof, the low surface energy layer includes at least one of gypsum and a cement as a binder, and the low surface energy layer includes at least one filler to establish a matrix composite, the filler including at least one of a ceramic, carbon black, carbon graphite, and a metal. In one embodiment, the hermetic coating includes a first layer consisting essentially of a polymer selected from di-p-xylylene and halogenated derivatives thereof, and the low surface energy layer enhances the homogeneity of the first layer.

In a number of embodiments, the medical device further includes at least one handling tag, each tag affixed to at least one of the substrate and a component, and each tag having a permeability characteristic at least as low as that of the hermetic coating. In some embodiments, the coating has at least first, second and third layers, and at least one of the first, second and third layers consists essentially of a polymer and at least one of the other two layers consists essentially of inorganic material such that each layer differs in at least one diffusion barrier property from the other layers and adds to an overall barrier effect of the coating. Preferably, a barrier property for the transport of impurities is dominated more by the interface between adjacent layers within the hermetic coating than by the thickness of each individual layer. In certain embodiments, the low surface energy layer and the hermetic coating conform to and cover at least substantially all of the components, and the medical device further includes a biocompatible protective layer deposited over the hermetic coating to minimize damage to the hermetic coating during handling of the medical device.

This invention also features a method of coating a three-dimensional object, including selecting an object having at least a first three-dimensional portion having a first surface, depositing a low surface energy layer on at least the first portion of the selected object utilizing a wet coating technique, and solidifying the low surface energy layer. The method further includes depositing a hermetic coating to conform substantially to the low surface energy layer.

In some embodiments, the low surface energy layer exhibits surface reduction of a factor ranging between 1 to 100 compared to the first surface, and the low surface energy layer has Young's modulus lower than 50 GPa. In certain embodiments, the low surface energy layer rounds the volume of surface features for the three-dimensional portion to have an average minimal radius between 10 to 1000 microns, and the low surface energy layer has hardness lower than 20 Vickers.

Preferably, the low surface energy layer exhibits less than twenty percent shrinkage during solidification.

In some embodiments, the low surface energy layer is selected from the group consisting of silicones, polyurethanes, gypsum, cements, epoxies, sol-gels, ethylene-vinyl acetate and mixtures thereof, the low surface energy layer includes at least one of gypsum and a cement as a binder, and the low surface energy layer includes at least one filler to establish a matrix composite, the filler including at least one of a ceramic, carbon black, carbon graphite, and a metal. In certain embodiments, the low surface energy layer is cured by at least one of ultraviolet radiation, heat and a chemical additive. In some embodiments, the low surface energy layer is deposited by at least one of spin coating, dip coating, screen-printing, spraying, casting and molding. In a number of embodiments, the method further includes pre-conditioning at least the first three-dimensional portion to improve adhesion for the low surface energy layer, such as by covering the first surface with at least one of an adhesive promoter and a plasma. In one embodiment, the hermetic coating includes a first layer consisting essentially of a polymer selected from di-p-xylylene and halogenated derivatives thereof, and the low surface energy layer enhances the homogeneity of the first layer.

In a number of embodiments, the object is a medical device which further includes at least one handling tag, each tag affixed to at least one of the substrate and a component, and each tag having a permeability characteristic at least as low as that of the hermetic coating. In some embodiments, the coating is applied in at least one set, each set having at least first, second and third layers, and at least one of the first, second and third layers consists essentially of a polymer and at least one of the other two layers consists essentially of inorganic material such that each layer differs in at least one diffusion barrier property from the other layers and adds to an overall barrier effect of the coating. Preferably, a barrier property for the transport of impurities is dominated more by the interface between adjacent layers within the hermetic coating than by the thickness of each individual layer. In certain embodiments, the low surface energy layer and the hermetic coating conform to and cover at least substantially all of the components and at least a portion of the handling tag, and the medical device further includes a biocompatible protective layer deposited over the hermetic coating to minimize damage to the hermetic coating during handling of the medical device. In certain embodiments, adhesion of the first adjacent layer is enhanced by at least one of a silanization, a plasma treatment of the first surface and an ionization of parylene.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

Figure 1:
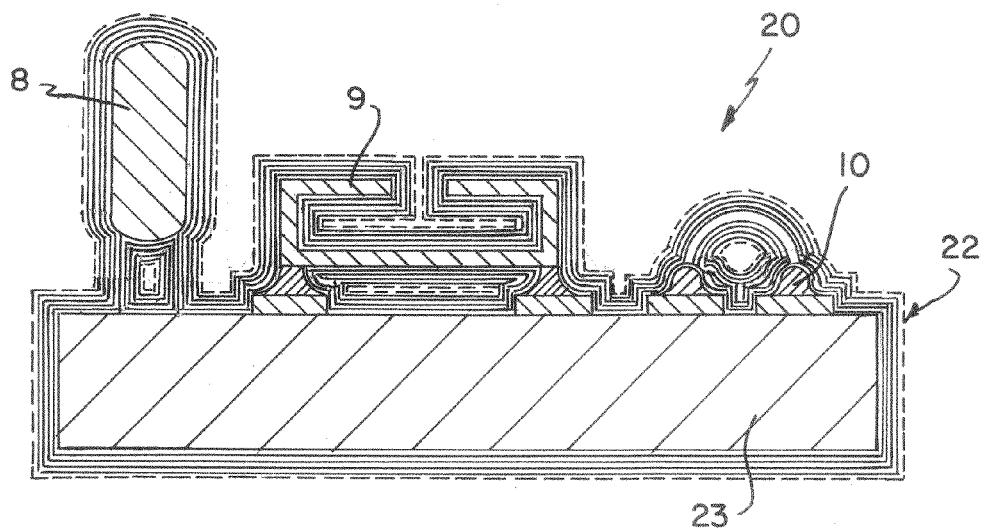
FIG. 1 is a schematic cross-sectional view of complex, three-dimensional components and a substrate coated with multiple layers according to the invention disclosed in U.S. Patent Application Publication No. 2011/0039050.

This invention may be accomplished by implantable medical devices, and methods of coating same, including a plurality of components disposed on a substrate, and a low surface energy layer deposited as a liquid over at least the first portion of the components and the substrate, the low surface energy layer becoming solidified after deposition. The devices further include a biocompatible hermetic coating conforming to and sealingly covering at least a portion of the low surface energy layer. Preferably, the hermetic coating has multiple layers with at least one layer consisting essentially of a polymer such as parylene and at least one of the other layers consisting essentially of inorganic material such that each layer differs in at least one diffusion barrier property from the other layers and adds to an overall barrier effect of the coating.

To improve both the conformity and stress release of the packaging, the inventors have conceived of an initial low surface energy layer especially suitable for multilayer hermetic coating of medical implants. The concept of the initial layer is based on a first liquid state or phase of a substance that minimizes the surface energy to achieve equilibrium, and a solidification of the liquid state or phase by a chemical process involving for example polymerisation or hydrolysis. Furthermore, in the liquid phase, the substance may enter the device cavities and seal them and further fill areas of negative slope before the solidification. Materials or substances with low volume reductions from liquid to solid phase, also referred to as low shrinking material, are preferred.

The advantage of using a low surface energy layer according to the present invention is first the improvement of security by increasing the conformity of the multilayer hermetic coating by volume rounding of the device accomplished by the low surface energy layer, especially for small feature size electronic encapsulation. In particular, the use of hermetic coatings composed of one or more inorganic layers, which tend to be much denser but less conformal than organic material, benefits of this improvement. Moreover, the low surface energy material, with a reduced free surface energy, shows a higher wetting of the device surface that overcomes fouling effects and guarantees the deposition in cavities and shadow regions. In addition, by a reduction of the surface, the low surface energy layer also release the stress on the adjacent layer and increase the mechanical stability of the device. Finally, the hardness and adhesion material properties used for the low surface energy layer are adapted to limit the fragment release of the medical device.

For the organic material that may compose the hermetic coating, parylene is preferably utilized because of its high conformity and biocompatibility. However, the deposition and durability of this material is dependent on the substrate material and its preconditioning, such as reported for different metals in "Transition Metals for Selective Chemical Vapor Deposition of Parylene-Based Polymers" by Vaeth at. al., Chem. Mater. 12, 1305-131 (2000). For the proposed invention, different types and compositions of components on the medical device are possible. As a consequence, the lack of homogeneity observed for the thin parylene film on such a device, composed of different materials, can be reduced by the use of one material only with the low surface energy layer according to the present invention. This implementation enhances the performance as well as the security of the packaging. The present invention is described in more detail below in relation to FIGS. 4-6.

FIG. 1 illustrates an example of components and a substrate of an implantable medical device 20 with three-dimensional conformal packaging according to the invention disclosed in U.S. Patent Application Publication No. 2011/0039050, shown without a low surface energy layer according to the present invention. Device 20 includes a plurality of three-dimensional components, such as transistor 8, micro-electro-mechanical system 9 and conductive bonding 10, on a substrate 23 which can be flexible or rigid as desired. A biocompatible multi-layer coating 22 applied by vapour deposition conforms to and sealingly covers at least a portion of the components 8,9,10 and the substrate 23.

Figure 2:
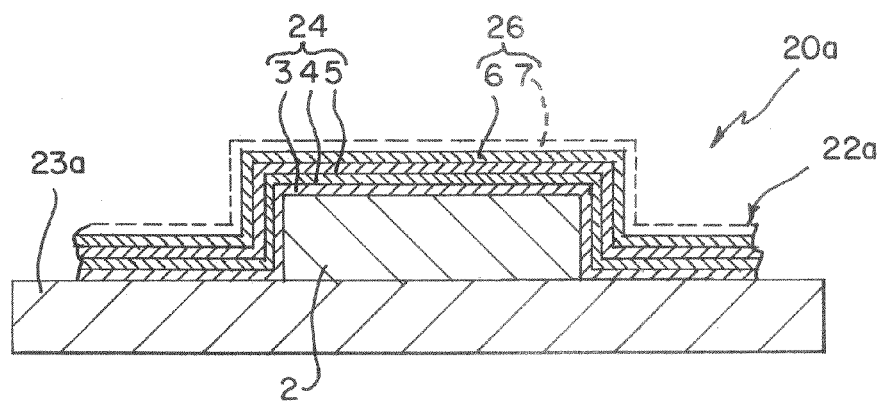
FIG. 2 is an enlarged cross-sectional view of multiple hermetic layers according to the prior invention protecting a component on a substrate.

The coating 22 is applied in at least two sets 24, 26, as illustrated schematically in FIG. 2, to form coating 22a over component 2 of device 20a with substrate 23a. Each set has at least first, second and third layers, such as layers 3, 4 and 5 of set 24. At least one of the first, second and third layers consist essentially of a polymer such as parylene and at least one of the other two layers of the set consist essentially of inorganic material such that each layer differs in at least one diffusion barrier property from the other layers in the set, for example differing in diffusion behaviour through each layer relative to the other layers. In some constructions, the barrier property for the transport of impurities, such as unwanted molecules, atoms or ions, both inward toward a packaged device as well as outward toward a patient in which the device is implanted, is dominated more by the interface between two adjacent layers than by the thickness of each individual layer. Preferably, the diffusion behaviour of each layer is additive to that of the other layers, and set 26 repeats the same sequence of layers with layers 6, 7, 7' (not shown) etc. As many sets of layers can be applied as desired. In some constructions, an additional treatment, such as a gas plasma, or an additional layer is added to improve the interface between two layers, especially with respect to impurity diffusion.

It is a realization of the inventors that increasing the number and type of thinner layers, rather than having fewer, thicker layers, enhances overall barrier properties of packaging due to the increased number of layer interfaces. In other words, the sum of the interfaces dominates diffusion behaviour, and therefore the overall barrier effect of the coating, more than the sum of the thicknesses of the layers. This may also be expressed as the diffusion barrier being composed by the layer interface and each layer itself. Polymers such as parylene are especially desirable for properties such as being pin-hole free, homogenous, and stress-free, and denser materials such as certain inorganic materials are especially desirable for their density.

Figure 3:
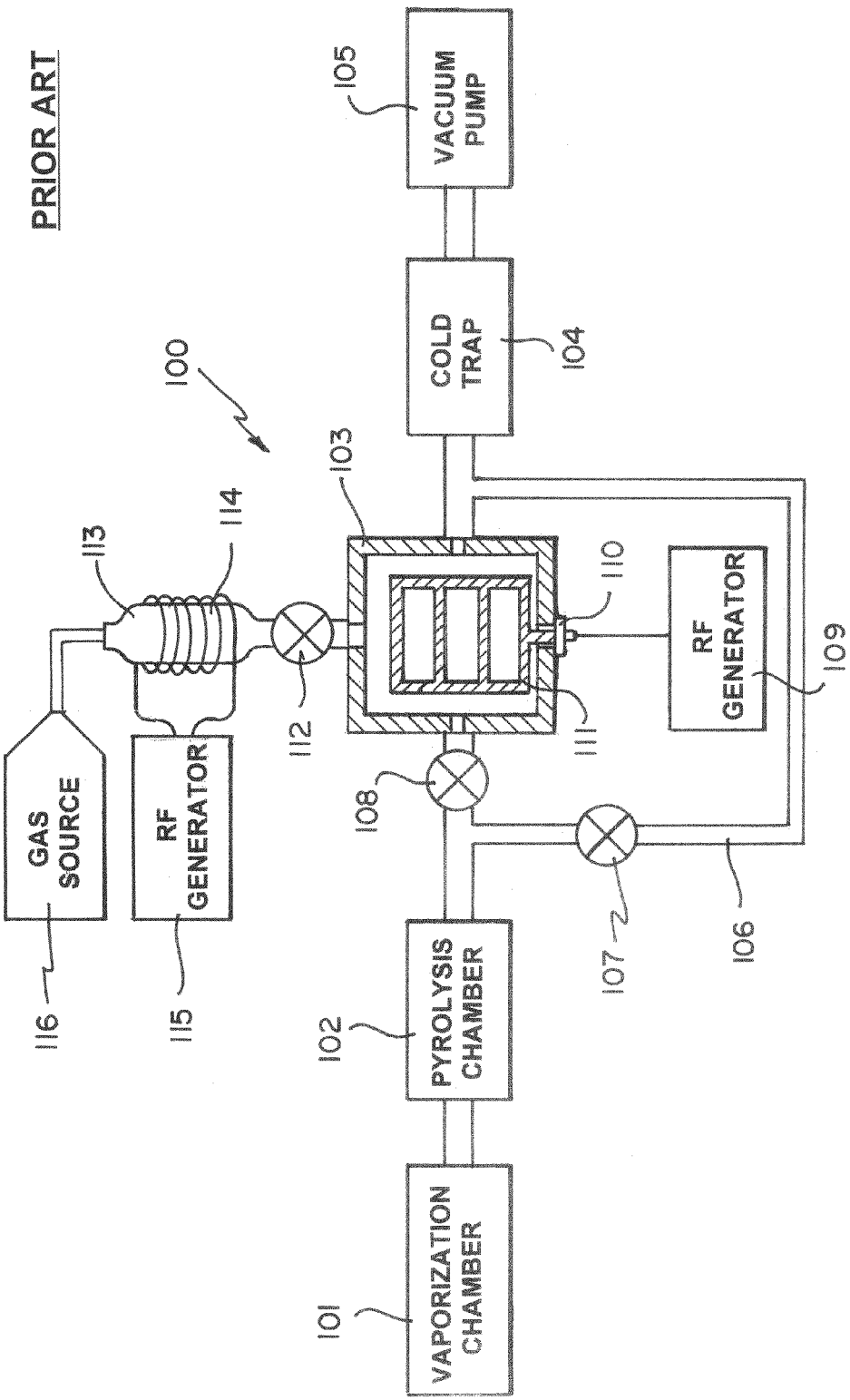
FIG. 3 is a schematic diagram of a reactor system for producing multi-layer packaging after an initial low surface energy layer is deposited according to the present invention.

One system 100 for achieving such conformal packaging with multi-layer coatings is shown in FIG. 3. Deposition chamber 103 can be utilized for a thermal process, such as a conventional Gorham process, or a plasma enhanced process. For the thermal process, such as for parylene deposition, a vaporization chamber 101 is provided to vaporize a solid parylene precursor, for example a stable di-cyclic dimer, di-p-xylylene, or halogenated derivatives at temperature between 110° and 200° C. The vaporized precursor then passes to a pyrolysis chamber 102 to decompose the dimer in reactive species, such as monomers, at temperatures between 400° C. and 700° C. For dichloro-p-xylylene, typical parameters are 150° C. for the vaporization and 650° C. for the pyrolysis. The pyrolyzed precursor then passes from the pyrolysis chamber through a gate valve 108 to the medical devices to be treated on a sample holder 111 in the deposition chamber 103. Typical parylene layer thickness is between 10 nm-100 microns. The precursor vapour pressure in the deposition chamber 103 is approximately between 1 and 10 Pa, typically 7 Pa, and the substrate temperature is substantially at room temperature. The remaining vapour mixture then passes from deposition chamber 103 to a cold trap 104 connected to a vacuum pump 105. During the parylene deposition, gate valves 107 and 112 are closed.

For the plasma enhanced process, the deposition process performed in chamber 103 can be either an external downstream plasma enhanced chemical vapour deposition (PECVD) facility or an in-situ plasma enhanced process. The downstream reactor is composed of a plasma tube 113 and a coil 114 around the plasma tube connected to the RF generator 115. The tube 113 is in gaseous communication with the gas source 116 and the deposition chamber 103. The desired amounts and proportions of gases supplied by gas source 116 introduced into the plasma tube 113 may be regulated using one or more mass flow controllers. The capacitively and/or inductively coupled high frequency plasma is utilized to excite and/or dissociate most of the entering process gas created by organic or inorganic precursors. This reactive gas is then injected in the deposition chamber 103 through a valve 112 that is alternatively opened and closed in counter phase with the gate valve 108 for parylene deposition. During the downstream deposition, the valve 107 is open to evacuate parylene via a bypass 106 to the cold trap 104. The power of the generator is between 10 to 500 Watts according to the specific reactor size.

For the in-situ plasma process, controlled plasma is formed adjacent to the medical device wafers by RF energy applied to sample holder 111 from RF generator 109, with the deposition chamber 103 grounded, via a high frequency sealed pass-through connector 110. RF generator 109 can supply a high RF frequency of typically 13.56 MHz or 2.45 GHz to the sample holder 111 to enhance the decomposition and/or excitation of reactive species introduced into chamber.

In a number of constructions, one of the inorganic layers is $SiN_x$ for its low permeability and low film stress characteristics. Typically, the deposition conditions are 130 sccm of $SiH_4$ (5% in argon), 20 sccm $NH_3$, 100-180 W RF power, 800 mTorr chamber pressure, and 80-120° C. substrate temperature. Preferably, thicknesses between 10-300 nm are deposited. Other gases could be used, as for example $SiH_4/NH_3/H_2$ or $SiH_4/N_2$.

In a number of constructions, one of the inorganic layers is $SiO_x$ for its well established process. Typically, the deposition conditions are 150 sccm $SiH_4$, 100 sccm $N_2O$, 30-80 W RF power, 800 mTorr pressure, and 80° C. substrate temperature. Preferably, thicknesses between 10-300 nm are deposited. Other gases could be used, as for example $SiH_4/N_2O/Ar$ or $HMDS/O_2$.

Other inorganic materials could be used as well according to the present invention, with biocompatibility being preferred. Possible materials including, but not limited to, metals, metal oxides, metal nitrides, metal carbides, metal oxynitrides, metal oxyborides, and combinations thereof can be utilized. Metals include, but are not limited to, titanium, aurum, platinum, argentum, ferrum, aluminum, nickel, indium, tantalum, tin, zirconium, chromium, zinc, barium, calcium, sodium, alloys thereof, and combinations thereof. Metal oxides include, but are not limited to a compound of oxygen and the metals mentioned above and combinations thereof. Some examples are titanium oxide, aluminum oxide, calcium oxide, sodium oxide, zirconium oxide. Metal nitrides include, but are not limited to a compound of nitrogen and the metals mentioned above and combinations thereof. Some examples are aluminum nitride titanium nitride. Metal carbides include, but are not limited to a compound of carbon and the metals mentioned above and combinations thereof. Metal oxynitrides include, but are not limited to a compound of oxygen, nitrogen and the metals mentioned above and combinations thereof. Other inorganic materials could be used, but not limited to, are semi-metals, semi-metal oxides, semi-metal nitrides, semi-metalcarbides, semi-metal oxynitrides and combinations thereof. Preferably materials are, but not limited to, silicon, germanium, boron, silicon oxide, silicon nitride, silicon oxynitride, germanium oxide, germanium nitride, germanium oxynitride, boron oxide, boron nitride, boron oxynitride and combinations thereof. Other inorganic biocompatible materials which can be deposited are calcium phosphate, barium sulfides, and barium oxysulfides.

The structure of the materials mentioned above could be crystalline, partially crystalline or amorphous. Preferably amorphous materials are based on, but not limited to, silicon, boron, carbon, titanium, aluminum, zirconium and hydroxylapatite and combinations thereof.

Layer on substrate adhesion or layer on layer adhesion could be improved by different processes. Typically for parylene adhesion, either on substrate or on layer, but not limited to, silanization or gas plasma treatment are used. For example oxygen, nitrogen or air plasma is applied directly in the deposition chamber 103 before coating. Further, other adhesion layer or plasma enhanced deposition layer can be used. Preferably, a well known adhesion layer based on silanes are composed of vinyl trichlorosilane in either xylene, isopropyl alcohol or a chlorofluorocarbon gas. Alternatively, gammamethacryloxypropyltrimethoxysilane in a methanol-water solvent have been successfully used. Silanes can also be vapour phase applied if non-liquid application is preferred.

Figure 4:
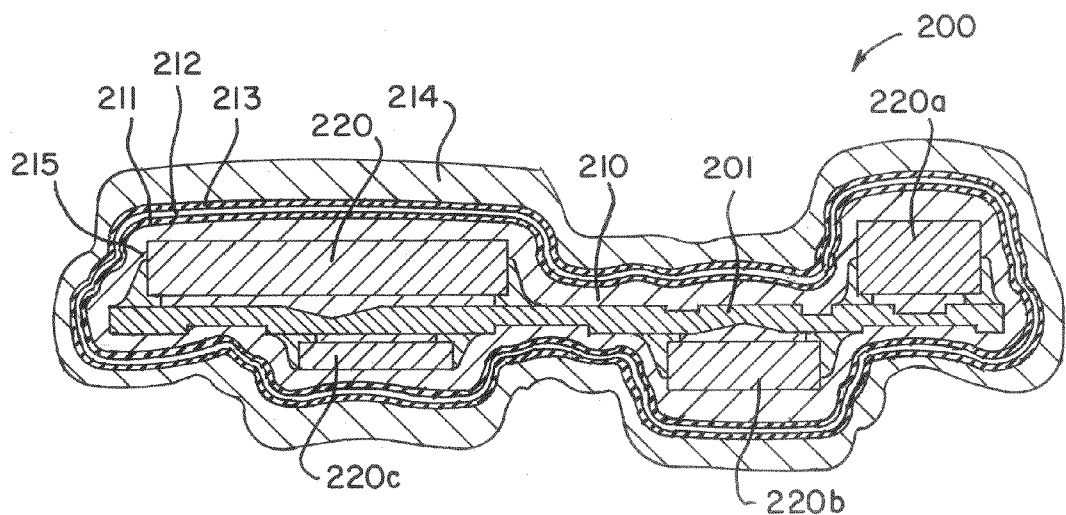
FIG. 4 is a schematic cross-sectional view of complex, three-dimensional components and a substrate coated with an initial low surface energy layer and a hermetic coating according to the present invention.

FIG. 4 illustrates an embodiment of an implantable device coated according to the invention. In this construction, device 200 that includes a plurality of three-dimensional components 220, 220a, 220b and 220c, such as for example transistors, micro-electro-mechanical systems, optical systems, energy harvesting systems, magnetic systems and a combination thereof that are integrated with conductive bonding 215 or otherwise fixated to a flexible substrate 201. In another construction, substrate 201 is substantially rigid. Substrate 201, components 220, 220a, 220b, and 220c, and bonding 215 are at least partially encapsulated with the packaging 210, 211, 212, 213, 214 as shown in the illustration. The packaging is composed by a low surface energy layer 210, a hermetic multilayer coating with layers 211, 212, 213, and a protective layer 214 to prevent handling damage. The preferred structure for the hermetic coating is a composition of organic and inorganic materials. A simple example of such a structure is the alternation of a first organic hermetic layer 211, with a second inorganic hermetic layer 212, and a third organic hermetic layer 213 to complete the hermetic coating, such as described above in relation to FIGS. 1-3.

The reduction of the surface energy of the layer 210 is due to the liquid-solid phase transition whereby first the liquid material tends to reduce its surface A with the volume rounding of the medical device and, second, this ideal scenario is preserved with the solidification of the material. In addition, low free surface energy a materials are utilized according to the present invention to enhance and, preferably, ensure a higher wetting on the device. These characteristics lead to a layer with a reduced total surface energy E, so-called low surface energy layer 210, as:

$$E = \sigma A \qquad \text{EQ. 1:}$$

As a consequence, the low surface energy layer 210 is not a continuous thin film of homogeneous thickness and the substance in the liquid phase may penetrate into cavities and areas of negative slopes to fill them before the solidification. In particular, small electronic feature sizes benefit from this phenomenon. The dynamic wetting of the surface by the liquid material also depends on the viscosity, with a better rounding effect corresponding to a higher viscosity. In contrast, a too high viscosity adds a too large volume for the packaging in comparison to the size of the medical device. As a result, an adaptation of the viscosity to complex topology structure of the device with viscosities typically between 100-200,000 mPas, but preferably 10,000-100,000 mPas are preferred.

The base materials used for the low surface energy layer 210 are typically silicones, polyurethanes, gypsum, cements, epoxies, sol-gels and combinations thereof, and are selected for the different device topology structure, compound materials and configurations. The conformal deposition of the low energy surface layer 210 to the medical device depends on the effect of the phase-transition from liquid to solid, especially shrinking. The term shrinking means that during the solidification, such as by polymerization or hydrolysis, for example, the initial volume is reduced, which may lead to crack formation or cavities. The ideal case of non-volume reduction from liquid to solid phase-transition is exhibited by substances of silicone rubber, especially PDMS (polydimethylsiloxane) and silicones, and gypsum materials including calcium sulphate ($CaSO_4$). Silicon rubber, a biocompatible elastomer material based on cross-linked siloxane backbones, is desirable for medical implants. Other functionalities such as hardness of hermeticity can be added to the polymers by replacing the methyl groups linked to the silicone backbone with other organic groups. The other more extensively used low shrinking biocompatible elastomer is polyurethane, including materials that incorporate a carbamate group, as well as other functional groups such as ester, ether, amide, and urea. These polymeric materials have good moisture resistance and preferably improve the total hermeticity and adhesion of the packaging.

For use as a low surface energy layer according to the present invention, hardening of these polymer materials with cross-linking of polymer chains is required in some cases, for example to ensure the handling of the medical device without packaging degradation. For this purpose, curing based on ultraviolet radiation, heat or chemical additive are performed. In addition, other physical properties such as, for example, adhesion and hermeticity are also influenced by the curing process. Siloxane-urethane copolymers are also developed for medical applications, to increase the toughness of silicone, with a typical amount of 5-25% by weight. As mentioned above, gypsum may also be used in regard to its minimal shrinkage and good biocompatible property. However, special care may be needed to avoid release of surface particles with this mechanically rather brittle substance. One possibility is to use gypsum as a binder for the polymers in order to improve the material strength, typically with an amount of less than 60% by weight, preferably less than 50% by weight, more preferably 0.1% to 30% by weight. Certain cements, especially biocompatible cements used in surgical applications based on gentacin sulphate, or dentistry based on glass-ionomer, also have low shrinking characteristic. Brittleness and low tensile and flexural strength has limited the uses of such material, but may also be used for a binder with typical amount of less than 70% by weight, preferably less than 50% by weight, more preferably 0.1% to 40% by weight in polymers. In other constructions, a matrix composite is established by adding at least one filler to at least one polymer. Suitable fillers include ceramic powder or nanopowder (typically less than 60% by weight, preferably 0.1% to 20% $SiO_2$, $Al_2O_3$, CaO, $CaCO_3$, MgO, $MgCO_3$, $TiO_2$, and $CrO_2$, for examples), carbon black or carbon graphite powder or nanopowder, or metallic powder or nanopowder. In certain constructions, UV (ultraviolet) curing or thermal curing is added in the deposition process to increase the adhesion. Another aspect includes adapting these materials to reduce the polymers water adsorption (swelling) by the selection of the appropriate particle size.

Epoxy resins, material containing three-membered rings known as the epoxy, epoxide, oxirane, or ethoxyline group, are also suitable for use according to the present invention. Most epoxy resins are cured with cross-linker that determines the chemical and physical properties of the substance. In particular, low shrinkage material and good dimensional stability of cured epoxy is induced by the reaction of groups that involves the opening of the ring. This material exhibits good mechanical strength and toughness, adhesion and moisture barrier characteristic. Adhesive materials based on epoxy silicone, epoxy polyurethane or acrylic are also suitable to increase the cohesion of the layer. Another aspect includes using the epoxy resin as a matrix composite, as for example adding silica fillers for ring opening of polymerization with a typical amount of 0.5% to less than 60% by weight, to reduce the shrinking of the curable material.

Finally, sol-gel materials are also useful for the low surface energy layer material. The processing is based on the formation of or semi-metal oxides by a hydrolysis of precursors in water, spontaneously or with the help of an acid or base catalysis. The precursors used in typical bio-encapsulation are an alkyl silicate, an alkoxymetallate or an alkoxysilane, or a combination thereof. Different forms appear during the condensation such as soluble, colloidal and finally phase separated polymers to form hydrogels. The removal to the liquid phase by processes such as extraction or drying, or a combination thereof, leads to a dry porous oxide xerogels material. The use of a porous material for the matching layer is to increase the diffusion path length and thus the hermeticity of the structure. The pore dimension is for this purpose the key parameter. Dense xerogels, with pore of 0.5-4 nm will be preferred. In another embodiment, layers composed by a combination of the colloids or the hydrogel or less denser xerogels with materials mentioned above or liquids are used.

The material based on copolymers and involving the technology of the melting EVA (Ethylene-Vinyl Acetate) in a vacuum furnace following by a subsequent application of Tefzel by DuPont (E.I du Pont de Nemours & Company), a commercially deployed brand name of ETFE (Ethylene Tetrafluoroethylene), or Teldar by DuPont, based on polyvinyl fluoride (PVF), layers is also used. This technique was successfully applied for long term UV resistive outdoor packaging of photovoltaic modules. Due to the surface reduction of the melting EVA in the vacuum oven, the substance penetrates into cavities. Finally, lamination of Tefzel or Teldar foil creates a highly resistive and chemically stable layer.

Figure 5:
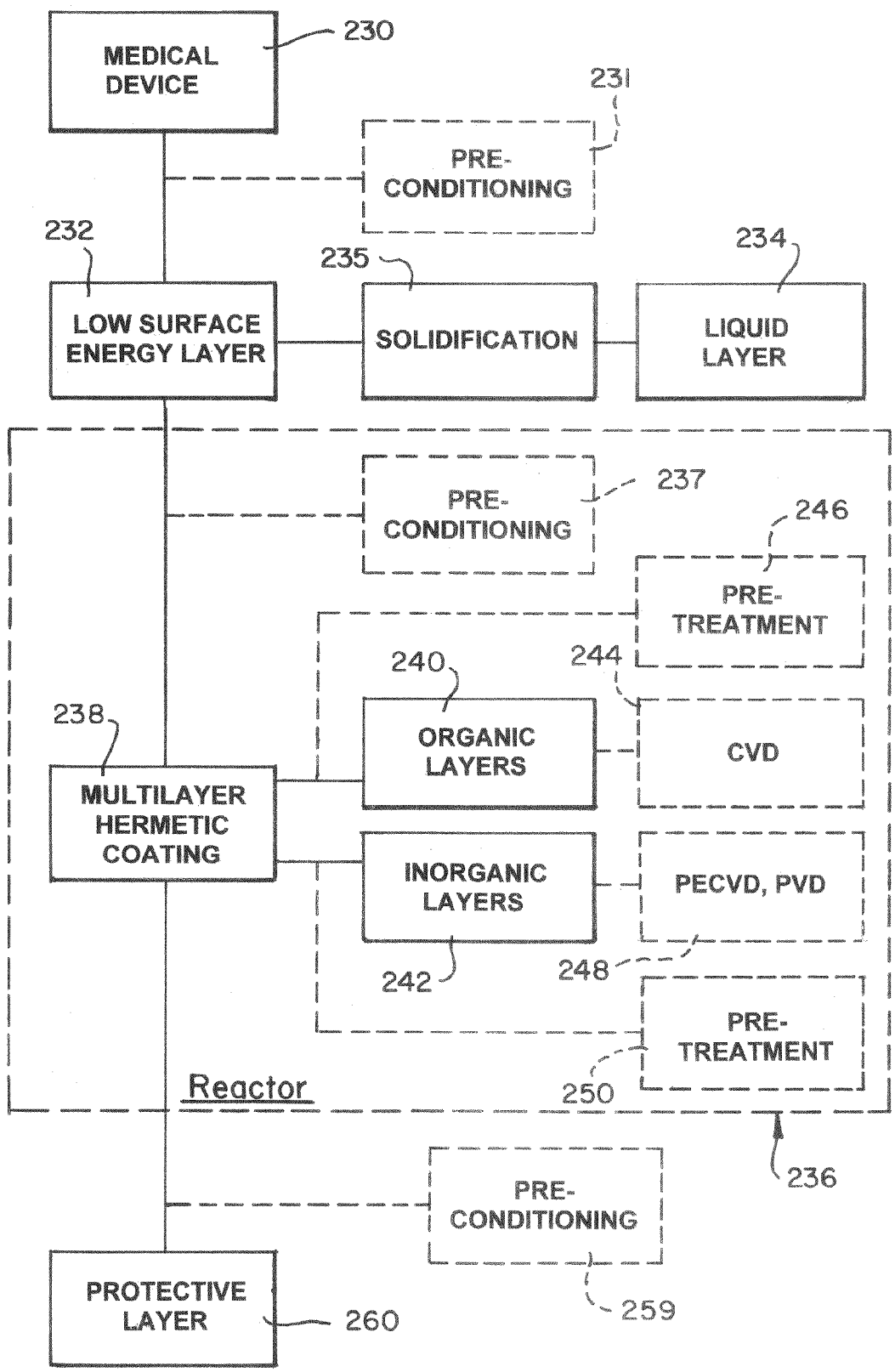
FIG. 5 is a flow chart illustrating one process according to the present invention for applying a low surface energy matching layer, followed by a multi-layer hermetic coating within the reactor system of FIG. 3 and then a protective layer.

One process according to the present invention is illustrated in FIG. 5. A medical device 230 is selected and optionally pre-conditioned, step 231. Pre-conditioning includes a cleaning process that can be made by a solvent, and may be followed with a treatment such as but not limited to a plasma activation or a silanization, and may be completed by an adhesive promoter deposition as, for example, a primer. One possible process during the plasma treatment with active gases is the addition of a polar functional group to the surface. Alternatively, silane functional groups can also be employed to promote the adhesion. Subsequently, as described above, a low surface energy layer is formed, step 232, by depositing a liquid layer, step 234 and solidifying it, step 235. The application of the low surface energy layer 232 depends on the technology that will be selected regarding to the complex topology structure of the device. In particular, for a flat surface and in order to reduce the packaging size, spin coating may be employed to reduce the thickness of the film and guarantee the homogeneity. More generally, the exterior surface of a medical device shows a complex structure, and dip-coating, screen-printing, spraying will be preferred for low-viscosity solutions, typically lower than 2000 mPas. For the higher viscosity, casting or moulding are used with a subsequent vacuum degassing. Heating of solutions to increase the mobility for a better wetting by decreasing the viscosity is also suitable in some embodiments.

A tumbling process is utilized in at least step 235 in some embodiments to limit the effect of gravity during layer formation to decrease the rounding of the low surface energy layer according to the present invention. In one embodiment, the movement of the particles, formation and growth during solidification from the liquid phase, and the polymer flow are averaged in terms of gravity influence in at least one direction. Rotations of the device in at least one axis, referred to herein as tumbling, is accomplished with spinning between 1-300 rpm (revolutions per minute), preferably between 5-30 rpm according to the particular substance and considering that a higher degree of polymerization or hydrolysis leads to a higher viscosity. In another embodiment, the mixing of the different substances are enhanced by the continuous rotation of the device. In yet another embodiment, homogeneity of binders or fillers with greater density than the local liquid density of the matrix substance is also preserved.

In the process illustrated in FIG. 5, all steps within dashed line 236 are conducted within a reactor, such as deposition chamber 103 of system 100 shown in FIG. 3 above. The low energy layer 232 is optionally pre-conditioned step 237, by silanization or plasma treatment and then a multilayer hermetic coating is fabricated, step 238, preferably with alternating organic layers 240 and inorganic layers 242. Deposition steps 244 and 246 of CVD (chemical vapor deposition) and plasma treatment are typically utilized to deposit organic layers 240 while deposition steps 248 and 250 of PECVD (plasma-enhanced chemical vapor deposition) or PVD (physical vapour deposition) and pretreatment preferably utilized to deposit inorganic layers 242. For example, between the layers 211, 212, and 213, FIG. 4, preconditionings 246 and 250, FIG. 5, of the surface to increase the adhesion is based on surface activation that may include, but is not limited to, a treatment with a plasma discharge. The gases used in the plasma discharge may include, but are not limited to, inert gases such as argon or nitrogen, or active gases such as oxygen, carbon dioxide, or methane. One of the processes occurring in the described environments is the cleaning by the use of reactive species. Another particular process consists of the production of radical sites to initiate covalent bounding. Another involved process is the dissociation of precursor molecules and the deposition of ultra-thin layer to improve the adhesion. Once a desired number of hermetic layers have been deposited, the device 230 is removed from the reactor. Preferably a protective layer 260 is then deposited with a pre-conditioning 259 including, but not limited to, a plasma activation or a silanization that may be completed by an adhesive promoter deposition, for example a primer being applied first.

In a preferred embodiment, parylene material is organic layer 240, FIG. 5, illustrated as organic material component 211, 213, FIG. 4, because of its high conformity and biocompatibility characteristics. Used as the first adjacent organic layer deposition on the low surface energy layer 210 homogenises the deposition thicknesses of the different compounds, as the parylene shows a high thickness discrepancy in the deposition on different materials and with different pre-treatment steps. For the adhesion of this first adjacent layer a pre-conditioning 237 to induce an increase of the surface energy as, for example, by a plasma treatment with active gases to add a polar functional group to the surface can be performed. Alternatively, silane functional groups can also be used to promote the adhesion. In yet another construction, ionization of parylene material by plasma can be used to increase the adhesion.

Materials used for inorganic material 242 may consist of, but are not limited to, silicon oxide or silicon nitride, chosen for theirs hermeticity and biocompatibility. The deposition may be based on organosilicone radicals coming from plasma decomposition of hexamethyldisiloxane (HMDSO) or hexamethyldisilazane (HMDSN).

The hermeticity concept of a multilayer structure is based on the following considerations. The inorganic thin film 212, FIG. 4, could provide sufficient hermetic packaging due to its high molecular density and intrinsic tightness. However, inorganic layers tend to create pinholes and non-uniform coatings on complex substrates. On the other hand, organic thin films, such as layers 211, 213, have proven to be pinhole free but have high permeability and reduced mechanical stability. Combination of the two different materials in a multilayer stack or set reduces the drawbacks of each other, and repeating this stack or set ensures an efficient hermetic barrier for medical implants. Multilayer hermetic coatings may be fabricated by one of the many procedures including, but not limited to, the procedure of the multilayer fabrication described in U.S. Pat. Application Publication Nos. 2011/0039050 and 2011/0038130.

The conformity of the packaging strongly depends on the much denser inorganic layer 212. The overgrowing behaviour of this layer on the implant, typically based on plasma process, is less conformal due to the directionality of the deposition and hence constitutes the conformity-limiting layer. When plasma is present, the electrons, more mobile than ions, diffuse from the plasma to the device to be coated, resulting in a plasma sheath between the more negative device potential and the more positive bulk plasma potential. One of the advantages is that the ions, present in the bulk plasma, feel an attractive electrostatic force and are accelerated to the implant, which can result in a higher density film due to the bombardment. One drawback in contrast is that the electron density can be inhomogeneous on three dimensional medical device structure, depending on the material and the surface topology, and leads to a deposition discrepancy. Another possible drawback consists of the presence of the plasma sheath region that space out the ionized atoms or molecules to be deposited from the bulk plasma to the device surface. This phenomenon is also a possible source of coating non-uniformities, with in particular a thicker deposition on device flat surfaces than in sidewalls. The separation of the ions to the device surface is related to the Debye length. This factor is a function to the electron density and the electron temperature that are strongly influenced by the electrode geometry, the RF power source and the gas pressure, and more generally to the condition or location of the plasma. In practical, these parameters enhanced the plasma sheath thickness by a larger factor than the Debye length, and in particular, the thickness increases strongly for gas pressure lower than 100 mbar. For increasing the security, the enhancement of the security margin related to the limited conformal ability of the inorganic layer 212 is performed with the volume rounding of the device guarantees with the low surface energy layer 210. To guarantee a sufficient overlap of the hermetic packaging, a volume rounding with minimal radius between typically 10 to 1000 µm are preferred.

In addition to an increase of the conformity, the low surface energy layer 210 acts as a stress releaser for the first adjacent organic layer 211. The physical significance of surface stress is the amount of reversible work per unit area needed to elastically stretch a pre-existing surface. The origin of the surface stress is due to physical and chemical changes in the substrate. In particular, the stress surface of a layer can be attributed to chemical bonds of surface atoms to the bulk of the layer. Due to the lower number of neighbours surrounding an atom in the surface compared to the bulk material, the local electron density in the surface is reduced. As a result to this non-uniform charge distribution, a different inter-atomic distance between atoms in the surface to the bulk compared to the inter-atomic distance in the bulk is observed. As a consequence, a compressive or tensile stress appears in addition to the free surface energy contribution in surface stress of solids, in contrast to what is shown for liquid or gas material, where the stress surface is equal to the free surface energy only. Inherently, the Young's modulus is related with the interaction energy and the atomic distance. In particular, the bending stress in a thin film of thickness $h_f$, deposited on a relatively thick substrate $h_s$, can be deduced by the standard equation derived from Stoney:

$$\sigma_S = R \frac{1}{6} \frac{E_S}{(1-v_S)} \frac{h_f^2}{h_S} \qquad \text{EQ. 2}$$

Where R is the curvature, $E_s$ is the Young's modulus, $v_s$ is the Poisson's ratio of the substrate. Assuming that the low surface energy layer 210 acts as a substrate for the thinner first adjacent organic layer 211, the surface stress is reduced for materials with a low Young's modulus. Young's modulus lower than 1 GPa ensures a better stress release and is preferably utilized for packaging with a higher permeability barrier. Higher Young's modulus of typically 1-10 GPa, in addition to high hardness of the material, typically between 1-20 Vickers are considered in order to be sure the rather stiffer inorganic layer 212 may not be damaged as soon as the device is even lightly handled, for example using tweezers or scalpels. In another hand, the surface stress is also modified by the thickness of the substrate $h_s$, considered in this particular case as uniform. However, the thickness $h_s$ of the low surface energy layer 10 can be replaced by the volume over surface ratio such as:

$$\sigma_S = R \frac{1}{6} \frac{E_S}{(1-v_S)} h_f^2 \frac{S}{V_S} \qquad \text{EQ. 3}$$

As shown with this example, the stress reduction is obtained for small surface S and high volume $V_s$ of the low surface energy layer 210. In order to guarantee a reasonable size of the total device, the volume $V_s$ is limited. To ensure a high mechanical stability of the implant, even with a complex device surface topology and a non-uniform thickness, a reduction of the surface of the device with the low surface energy layer 210 by a factor typically between 1-100 are used, preferably between 1-10.

To complete the packaging structure, preferably a protective layer 214, FIG. 4, also called stress buffer coating, is deposited on top of the hermetic multilayer coating, as illustrated in step 260, FIG. 5. The main requirement of the materials used for the protection is a high biocompatibility. For example, a suitable silicone rubber material is BIO-PSA 7-4560 Silicone Adhesive available from Vesta Inc., produced through a condensation reaction of a silanol end-blocked PDMS with a silicate resin. Benzocyclobutene (BCB) based polymer, used in intracortical neural implants, is also a possible suitable material to complete the structure. Other possibilities involving polyamide, polyimide or polyurethane biocompatible polymer materials. Finally, material used for the encapsulation of biological based on sol-gel technology is also possible.

Figure 6:
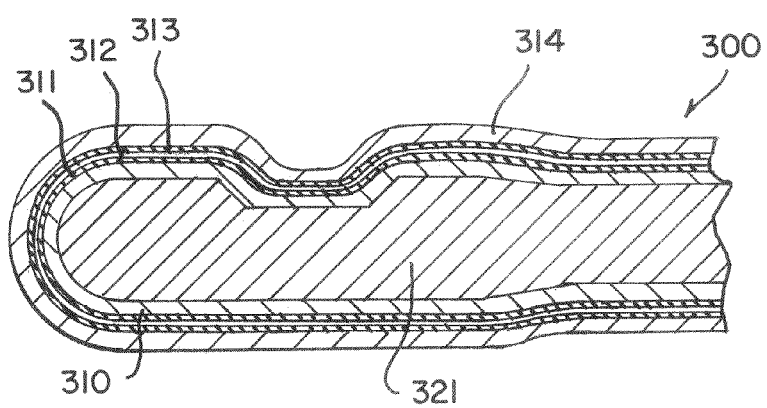
FIG. 6 is a schematic cross-sectional view of a different, non-electronic type of device with a coating according to the present invention.

It is not a limitation of this invention to coat medical devices with electronic components. For example, FIG. 6 illustrates another embodiment 300, where the packaging surrounds a three-dimensional substrate 321 to protect it against corrosion, such as, but not limited to, electrodes, magnet or metal, or against deterioration, such as for example for plastic pre-encapsulation. The packaging is composed of a low surface energy layer 310, a hermetic multilayer coating having at least layers 311, 312, 313, and a protective layer 314 to prevent handling damage.

Entire encapsulation of a medical device with a homogeneous and hermetic packaging film is difficult in practice. During deposition, parts of the medical implant in contact with one or more features of a holder are not coated by the hermetic protection layers. Therefore, the inventors propose the use of one or more biocompatible protection tags integrated to the medical device in contact to the manipulation tool during the deposition process. In this configuration, the surrounding implant packaging film exhibits defects only in the biocompatible handling plate. Because the hermeticity of the handling plate is higher than the one of the packaging film, defects in the packaging film on top of the handling plate do not affect the hermeticity of the entire encapsulation film.

Figure 7:
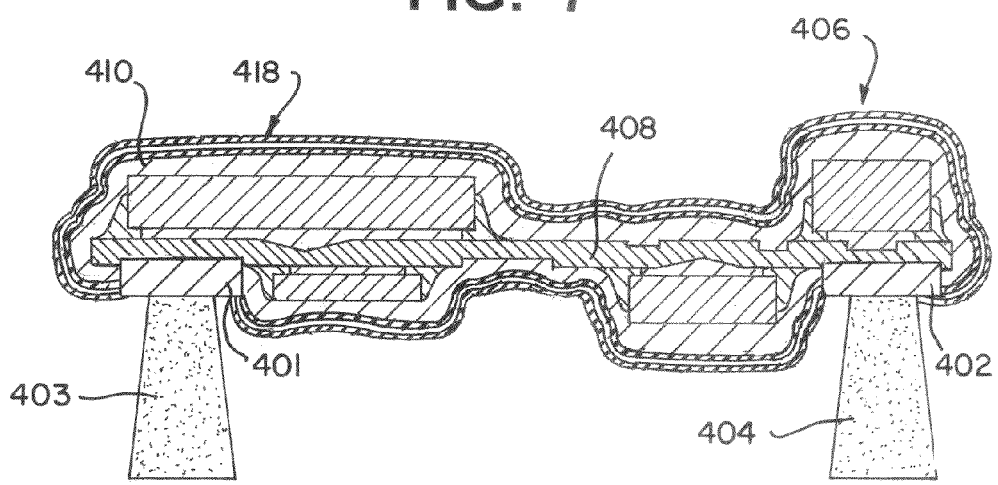
FIG. 7 is a schematic cross-sectional view of a device having a plurality of handling tabs according to the present invention resting on holders within a reactor system.

A simple method to guarantee the complete hermetic and homogeneous encapsulation of the medical device by the hermetic multilayer coating, for example in a plasma environment, is illustrated in FIG. 7. A plurality of biocompatible protection tags 401 and 402 are bonded or otherwise affixed to substrate 408 of the medical implant 406. The tags 401, 402 are composed of, for example, titanium or steel and allow holders 403, 404 to touch and support the device 406 during the deposition of a packaging film such as low surface energy layer 410 and hermetic layers 418, as well as guarantees the hermeticity of the non-covered areas where the holders 403, 404 touch the device 406, such as depicted in FIG. 7. The permeation properties of the tags has to be equal or lower than the permeation of the hermetic barrier layers 418 to guarantee the entire hermeticity of the barrier layers. An important property of the protection tags is a good mechanical resistance, to prevent the damage of the tags 401, 402 by the holders 403, 404. These protection tags can be precut and may then be glued by epoxy or silicone, bonded, or otherwise fixated onto the medical implant. In the particular case of deposition of one hermetic layer is based on plasma technology, the holder may be placed on the electrode that host the samples, or be part of this electrode. Other functionalities, such as using the tags 401, 402 for the final device handling by tweezers or scalpels, or adding mechanical resistance to the implant or local device protection of this later, may be implemented as well. In some constructions, the tags have one or more projections, tabs or other features to assist grasping and manipulation. In certain constructions, the tags are utilized to handle the device for a tumbling process, such as described above. In other constructions, to reduce the size of the device, tags 401, 402 are thin and may consist of foils or films, based on for example sputtering, physical- or chemical vapor deposition techniques.

Figure 8:
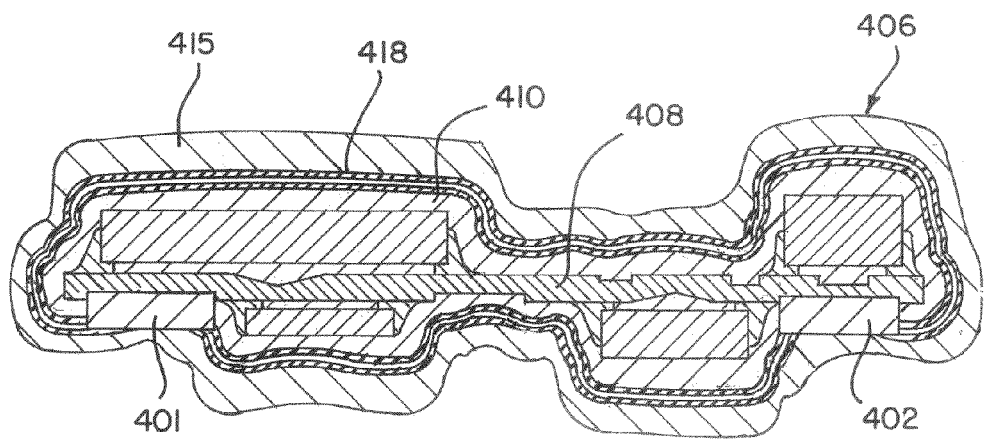
FIG. 8 is a schematic cross-sectional view of the device of FIG. 7 after removal from the reactor system and with a protective coating.

Device 406 is shown in FIG. 8 after it has been removed from a reactor and a protective coating 415 has been added, in some constructions totally covering the entire device including tags 401 and 402 as illustrated.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An implantable medical device comprising:
   a plurality of components disposed on a substrate having at least a first three-dimensional portion with a first surface;
   a low surface energy layer deposited as a liquid over at least the first portion of the components, the low surface energy layer becoming solidified after deposition and covering at least the first portion of the components; and
   a biocompatible hermetic coating conforming to and sealingly covering at least the low surface energy layer,
   wherein the low surface energy layer reduces the stress of the hermetic coating to improve adhesion of a subsequent layer by relieving stress.

2. The medical device of claim 1 wherein the low surface energy layer exhibits surface reduction of a factor ranging between 1 to 100 compared to the first surface.

3. The medical device of claim 1 wherein the low surface energy layer has Young's modulus lower than 50 GPa.

4. The medical device of claim 1 wherein the low surface energy layer rounds the volume of surface features for the three-dimensional portion to have an average minimal radius between 10 to 1000 microns.

5. The medical device of claim 1 wherein the low surface energy layer has hardness lower than 20 Vickers.

6. The medical device of claim 1 wherein the low surface energy layer has a composition which exhibits shrinkage during solidification lower than 20 percent.

7. The medical device of claim 1 wherein the low surface energy layer is selected from the group consisting of silicones, polyurethanes, gypsum, cements, epoxies, sol-gels, ethylene-vinyl acetate and mixtures thereof.

8. The medical device of claim 7 wherein the low surface energy layer includes at least one of gypsum and a cement as a binder.

9. The medical device of claim 7 wherein the low surface energy layer includes at least one filler to establish a matrix composite, the filler including at least one of a ceramic, carbon black, carbon graphite, and a metal.

10. The medical device of claim 1 wherein the hermetic coating includes a first layer consisting essentially of a polymer selected from di-p-xylylene and halogenated derivatives thereof, and the low surface energy layer enhances the homogeneity of the first layer.

11. The medical device of claim 1 further including at least one handling tag, each tag affixed to at least one of the substrate and a component, and each handling tag having a permeability characteristic at least as low as that of the hermetic coating.

12. The medical device of claim 11 wherein a protective coating covers the entire device including the tags.

13. The medical device of claim 1 wherein the coating has at least first, second and third layers, and at least one of the first, second and third layers consisting essentially of a polymer and at least one of the other two layers consisting essentially of inorganic material such that each layer differs in at least one diffusion barrier property from the other layers and adds to an overall barrier effect of the coating.

14. The medical device of claim 13 wherein a barrier property for the transport of impurities is dominated more by the interface between adjacent layers within the hermetic coating than by the thickness of each individual layer.

15. The medical device of claim 1 wherein the low surface energy layer and the hermetic coating conform to and cover at least substantially all of the components.

16. The medical device of claim 1 further including a biocompatible protective layer deposited over the hermetic coating to minimize damage to the hermetic coating during handling of the medical device.

* * * * *